United States Patent
Bosetti et al.

(10) Patent No.: US 11,021,416 B2
(45) Date of Patent: Jun. 1, 2021

(54) PROCESS FOR THE PRODUCTION OF OLEFINIC COMPOUNDS AND A HYDROCARBON FUEL OR A FRACTION THEREOF

(71) Applicant: versalis S.p.A., San Donato Milanese (IT)

(72) Inventors: Aldo Bosetti, Vercelli (IT); Sergio Francantonio Lombardini, Milan (IT); Gianni Girotti, San Giuliano Milanese (IT)

(73) Assignee: versalis S.p.A., San Donato Milanese (IT)

( * ) Notice: Subject to any disclaimer, the term of this patent is extended or adjusted under 35 U.S.C. 154(b) by 0 days.

(21) Appl. No.: 15/028,780

(22) PCT Filed: Dec. 24, 2014

(86) PCT No.: PCT/IB2014/067310
§ 371 (c)(1),
(2) Date: Apr. 12, 2016

(87) PCT Pub. No.: WO2015/101909
PCT Pub. Date: Jul. 9, 2015

(65) Prior Publication Data
US 2016/0251278 A1    Sep. 1, 2016

(30) Foreign Application Priority Data

Dec. 30, 2013   (IT) .......................... MI2013A002221

(51) Int. Cl.
*C07C 1/207* (2006.01)
*C10G 3/00* (2006.01)
(Continued)

(52) U.S. Cl.
CPC ............ *C07C 1/2078* (2013.01); *C07C 1/207* (2013.01); *C07C 7/04* (2013.01); *C07C 67/03* (2013.01);
(Continued)

(58) Field of Classification Search
None
See application file for complete search history.

(56) References Cited

U.S. PATENT DOCUMENTS

2004/0230085 A1* 11/2004 Jakkula .................... C10G 3/45
585/240
2008/0163543 A1*  7/2008 Abhari ................... C10G 45/60
44/308
(Continued)

FOREIGN PATENT DOCUMENTS

JP      2010-70651 A     4/2010
JP      2011-526640      10/2011
(Continued)

OTHER PUBLICATIONS

International Search Report dated Apr. 28, 2015 in PCT/IB2014/067310 filed Dec. 24, 2014.
(Continued)

*Primary Examiner* — Philip Y Louie
(74) *Attorney, Agent, or Firm* — Oblon, McClelland, Maier & Neustadt, L.L.P.

(57) ABSTRACT

The present invention relates to a process for the production of olefinic compounds that can be used for the production of detergents, additives, lubricants and/or plastic materials, or components which can be used in the field of oil explorations and productions, and a hydrocarbon fuel or a fraction thereof, which comprises subjecting a mixture of glycerides having at least one unsaturated hydrocarbon chain, to metathesis reaction and, after separating the olefinic mixture
(Continued)

obtained, effecting a hydrodeoxygenation and subsequently hydroisomerization process, so as to obtain the hydrocarbon fuel or a fraction thereof.

21 Claims, 1 Drawing Sheet

(51) Int. Cl.
| | |
|---|---|
| C07C 67/333 | (2006.01) |
| C07C 67/03 | (2006.01) |
| C10L 1/02 | (2006.01) |
| C11C 3/14 | (2006.01) |
| C11C 3/00 | (2006.01) |
| C07C 7/04 | (2006.01) |
| C10G 45/60 | (2006.01) |
| C10L 1/04 | (2006.01) |

(52) U.S. Cl.
CPC .............. *C07C 67/333* (2013.01); *C10G 3/45* (2013.01); *C10G 3/46* (2013.01); *C10G 3/47* (2013.01); *C10G 3/48* (2013.01); *C10G 3/50* (2013.01); *C10G 45/60* (2013.01); *C10L 1/026* (2013.01); *C10L 1/04* (2013.01); *C11C 3/00* (2013.01); *C11C 3/003* (2013.01); *C11C 3/14* (2013.01); *C07C 2523/46* (2013.01); *C10G 2400/04* (2013.01); *C10G 2400/08* (2013.01); *C10G 2400/22* (2013.01); *C10L 2200/0469* (2013.01); *C10L 2270/026* (2013.01); *C10L 2270/04* (2013.01); *Y02E 50/10* (2013.01); *Y02P 30/20* (2015.11); *Y02T 50/678* (2013.01)

(56) References Cited

U.S. PATENT DOCUMENTS

| | | |
|---|---|---|
| 2009/0250376 A1 | 10/2009 | Brandvold et al. |
| 2010/0160506 A1 | 6/2010 | Wu et al. |
| 2011/0027842 A1* | 2/2011 | Nielsen .................. C12P 7/6454 435/134 |
| 2011/0113679 A1* | 5/2011 | Cohen .................... C10G 45/00 44/388 |
| 2012/0165581 A1 | 6/2012 | Dupassieux et al. |
| 2012/0197031 A1 | 8/2012 | Firth et al. |
| 2012/0209017 A1 | 8/2012 | Ouni et al. |
| 2013/0236938 A1* | 9/2013 | Vander Hoff .......... C10G 33/06 435/134 |
| 2014/0243541 A1 | 8/2014 | Ouni et al. |

FOREIGN PATENT DOCUMENTS

| | | |
|---|---|---|
| JP | 2012-530149 A | 11/2012 |
| JP | 2013-507441 A | 3/2013 |

OTHER PUBLICATIONS

J.C. Mol., "Catalytic Metathesis of Unsaturated Fatty Acid Esters and Oils", Topics in Catalysis, Kluwer Academic Publishers-Plenum Publishers, vol. 27, No. 1-4, XP019292022, Feb. 1, 2004, pp. 97-104.

Office Action dated Jan. 31, 2019 in Japanese Patent Application No. 2016-539034, 8 pages (with English translation).

* cited by examiner

PROCESS FOR THE PRODUCTION OF OLEFINIC COMPOUNDS AND A HYDROCARBON FUEL OR A FRACTION THEREOF

The present invention relates to a process for the production of olefinic compounds and a hydrocarbon fuel or a fraction thereof, which comprises subjecting a mixture of glycerides having at least one unsaturated hydrocarbon chain to metathesis reaction and, after separating the olefinic mixture obtained, effecting a hydrodeoxygenation and subsequently hydroisomerization process, so as to obtain the hydrocarbon fuel or a fraction thereof.

This process advantageously allows both olefinic compounds to be obtained, which can be used, for example, as intermediates for the production of detergents, additives, lubricants and/or plastic materials or components which can be used in the field of oil explorations and productions, and also a hydrocarbon fuel, or fraction thereof, preferably selected from diesel, naphtha, jet-fuel or mixtures thereof.

Due to a decrease in fuel reserves of a fossil origin and the negative impact on the environment produced by anthropogenic emissions of carbon dioxide ($CO_2$), technologies aimed at producing fuels starting from biomasses (so-called bio-fuels), allowing, with time, the complete transition to renewable energy sources, are becoming increasingly more important.

Among the new sustainable energy sources, biomasses can significantly contribute to achieving these objectives. Biomasses are biodegradable vegetable or animal substances deriving from agriculture, forestry and all relative industries, comprising fishing, aquaculture and waste and scraps coming from the same.

At the same time, the need for breaking free from fossil sources alone and from the legislative obligations imposed on emissions of an anthropogenic origin, is also felt in the production of chemicals, indispensable for everyday life.

Consequently, the use of renewable sources such as biomasses, which are economical and sustainable from an environmental point of view, can offer an alternative to the use of fossil sources for the production of chemical products useful in everyday life (biochemicals, which refers to their production starting from renewable sources).

The development of so-called "green chemistry" is therefore underway, which implies a restructuring of the production chains through the use of renewable sources deriving from natural biomasses and transformation technologies with low environmental emissions, leading to the creation of so-called "bio-refineries".

The process of the present invention can be advantageously effected in a bio-refinery, by integrating the production of bio-fuels with the production of intermediates useful for the production of detergents, additives, lubricants and/or plastic materials or components that can be used in the field of oil explorations and productions (bio-chemicals), starting from the same renewable raw material, i.e. a mixture of glycerides, preferably of a vegetable or animal origin or of a microbial origin.

In the present invention, the integrated production of bio-fuels and bio-chemicals is obtained through a process which comprises a metathesis reaction followed by conversion of a part of the metathesis products.

At present, the production of bio-fuels from renewable sources, such as natural oils, is essentially effected through two main processes:

I. transesterification, mainly with methanol, with the production of FAME (fatty acid methyl esters), normally called bio-diesel; or II. through catalytic processes such as so-called "hydrotreating", with the production of paraffinic cuts, mainly diesel, but also gasoline, in variable proportions according to the processes used.

In the former case, a biofuel is obtained, which however has various problems (for example, unsatisfactory low-temperature performances, relating to instability in storage and distribution, etc.).

In the latter case, the starting oils are converted into hydrocarbon cuts with high performances, for example complete miscibility with refinery cuts from fossil sources, high engine features such as cold properties and high cetane number, etc. Among the numerous hydrotreating technologies available, the Ecofining™ process of ENI/UOP, can be cited, as described, for example, in patent applications WO2008/058664, EP1728844, WO2009/039347, WO2009/039335, WO2009039333, WO2009/158268 and in American patent U.S. Pat. No. 7,915,460, all in the name of ENI S.p.A. and UOP 11c, wherein all the documents are incorporated herein as reference. The main product of the Ecofining technology is called Green Diesel and can be obtained with yields of up to 88% with respect to the starting oil, or renewable source. The Ecofining process, starting from natural oil, typically leads to the formation (by weight) of 4-5% of propane, 1-8% of naphtha cut, 75-85% of diesel cut with about 1.5-3.8% of hydrogen consumption with respect to 100 of the starting biomass.

The hydrotreating process, in particular called Ecofining, is a two-step process: the first step consists in a hydrogenation/deoxygenation (hydrodeoxygenation) reaction which removes all the heteroatoms in the molecules, whereas the second step is a hydroisomerization/cracking step which allows a diesel cut to be produced, having the desired characteristics. In the first step, the catalytic system effects not only a deoxygenation of the feedstock (reduction of the esters to hydrocarbons), but also hydrogenates all the possible double bonds present in the fatty acids, whose esters form the starting oil. Consequently, the more unsaturated the starting mixture of fatty acids, the higher the specific hydrogen consumption of the catalytic hydrotreating process, will be.

Possible feeding streams for catalytic hydrotreating processes composed of completely saturated oils therefore represent particularly valuable feeds for said processes and in particular for the Ecofining process. The natural oils that can be obtained from cultivations, for example, are in fact a mixture of fatty acids in which the amount of unsaturated acids is not negligible.

More specifically, it would be desirable for these processes to have a feeding stream obtained by the selective transformation of the unsaturated components present in the starting renewable source alone, wherein the saturated components initially present have been left unaltered.

An objective of the present invention therefore relates to a process for the production of olefinic compounds and a hydrocarbon fuel or a fraction thereof, which comprises:

(a) subjecting a mixture of glycerides having at least one unsaturated hydrocarbon chain, possibly in a mixture with free fatty acids, to a metathesis reaction with at least one $C_2$-$C_6$ mono-olefin in the presence of a metathesis catalyst, so as to obtain a mixture of glycerides having at least one unsaturated hydrocarbon chain with a length less than the initial length, and a mixture of $C_6$-$C_{18}$ olefins;

(b) separating the mixture of $C_6$-$C_{18}$ olefins from the mixture of glycerides obtained in step (a);

(c) possibly subjecting the mixture of glycerides obtained in step (b) to a transesterification reaction with an alcohol selected from methanol, ethanol or mixtures thereof, so as to obtain a mixture of methyl and/or ethyl esters and glycerol;

(d) subjecting the mixture of glycerides obtained in step (b) or the mixture of methyl and/or ethyl esters obtained in step (c) to a hydrodeoxygenization process and followed by a hydroisomerization process, so as to obtain the hydrocarbon fuel or fraction thereof.

In the process described above, step (c') can be present, after step (c), wherein the glycerol is separated from the mixture of methyl and/or ethyl esters, and subsequently step (c'') wherein the methyl and/or ethyl esters having an unsaturated hydrocarbon chain are separated from the methyl and/or ethyl esters having a saturated hydrocarbon chain. The methyl and/or ethyl esters having a saturated hydrocarbon chain thus obtained are then subjected to the catalytic hydrodeoxygenation step (d) and subsequent catalytic hydroisomerization.

In particular, the hydrocarbon fuel or fraction thereof, produced with the process of the invention, is selected from: diesel, naphtha, jet-fuel, or mixtures thereof.

The mixture of $C_6$-$C_{18}$ olefins obtained from step (b) and/or the methyl and/or ethyl esters having an unsaturated hydrocarbon chain obtained from step (c'') are preferably intermediates that can be used for the renewable production (wherein "renewable production" refers to "production starting from renewable sources, alternative to fossil sources) of detergents, additives, lubricants and/or plastic materials or components that can be used in the field of oil explorations and productions.

The glycerides having at least one unsaturated hydrocarbon chain used in the mixture in step (a) are glycerides, preferably triglycerides, of a vegetable or animal origin or of a microbial origin.

As indicated in US2009/0077865 paragraph [009], the term fats and renewable oils comprises glycerides and free fatty acids, wherein the glycerides are mainly triglycerides, but monoglycerides and triglycerides can also be present.

Said glycerides of a vegetable or animal origin or of a microbial origin are preferably glycerides of fatty acids having at least one mono- or poly-unsaturated $C_{12}$-$C_{24}$ hydrocarbon chain.

The glycerides used in the process of the invention are preferably selected from: vegetable oils, such as: sunflower, rapeseed, canola, palm, soya bean, hemp, olive, linseed, mustard, peanut, castor, coconut and tall oil; recycled oils and/or fats from the food industry; lipids coming from algal cultivations; animal oils or fats, such as: lard, lard cream, tallow, milk fats; or mixtures thereof.

The metathesis reaction effected in step a) consists in a particular re-arrangement of the substituents present on one or more double bonds. If the reaction is attributed to the double bonds of a single olefin, this is known as homo-metathesis. If, on the other hand, it is attributed to a mixture of two or more olefins, this is called co-metathesis. The latter is of particular interest with regard to the present invention and can be schematized as follows:

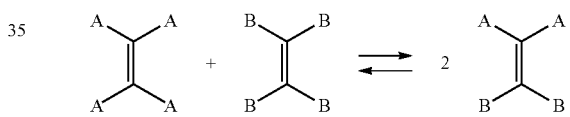

In the case of oils, the most favourable option is their co-metathesis with a short olefin ($C_2$-$C_6$). By considering, for the sake of simplicity, only the co-metathesis of esters of oleic acid (generally the most abundant among the unsaturated compounds present in vegetable oils) with ethylene, the reaction gives a mixture of esters of 9-decen-1-oic acid and 1-decene:

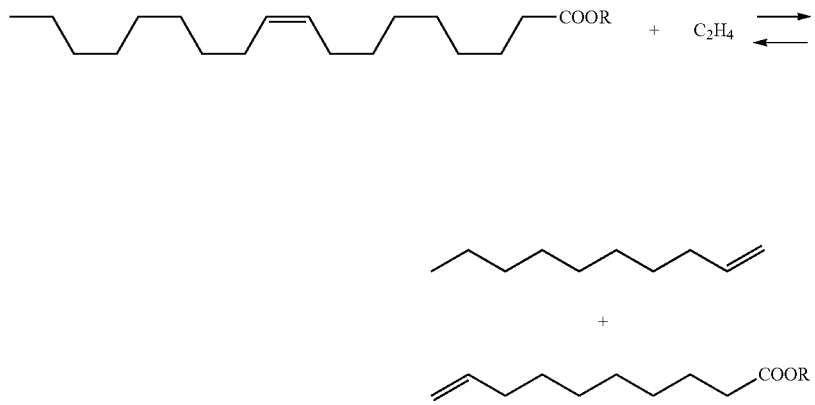

In practice, due to the presence in the starting oil of esters of other unsaturated acids such as linoleic and linolenic acids, the products obtained are esters of 9-decen-1-oic acid and a mixture of $C_4$-$C_{10}$ α-olefins and 1,4-pentadiene, in addition to the saturated fraction to be fed to the hydrotreating process. If the co-metathesis reaction were carried out with olefins different from ethylene, the distribution of the products obtained would be considerably different. With 1-butene, for example, there would be a mixture of esters of unsaturated $C_{10}$-$C_{13}$ acids, of $C_4$-$C_{13}$ olefins, terminal and internal, and olefins containing from 5 to 9 carbon atoms.

The olefin used in the metathesis process of the present invention is a $C_2$-$C_6$, preferably $C_2$-$C_4$, mono-olefin, selected from: ethylene, propene, 1-butene, but-2-ene, 2-methyl-propene, or mixtures thereof.

The molar ratio between the double bonds of the mixture of glycerides having at least one unsaturated hydrocarbon chain and the double bonds of said at least one $C_2$-$C_6$ olefin used in step a) preferably ranges from 1:0.1 to 1:20.

Furthermore, the preferred conditions for carrying out step (a) are a temperature ranging from 20 to 120° C., for a time ranging from 0.5 to 6 hours, preferably from 20 to 80° C. and 0.5 to 3 hours.

Step (a) is preferably carried out at a pressure ranging from 1 to 30 bars and even more preferably the pressure ranges from 1 to 15 bars.

The metathesis reaction is catalyzed by some transition metals such as, for example, ruthenium, molybdenum, osmium, chromium, rhenium and tungsten.

The metathesis catalyst of step (a) can be a carbene complex of a transition metal of Group 8, in particular selected from: ruthenium, molybdenum, osmium, chromium, rhenium, tungsten.

The catalysis of step a) can be either homogeneous or heterogeneous.

The metathesis catalysts that can be used in the present invention are, for example, those described in international patent application in the name of Elevance Renewable Science Inc. publication number WO2008/046106 and in international patent application in the name of Materia Inc. WO2008/08440, both incorporated herein as reference. In particular, the catalysts described in WO2008/046106, from page 15 paragraph [0061] to page 35 paragraph [106], and those described in WO2008/08440, from page 20 paragraph [0068] to page 39 paragraph [0020], can be used.

Other metathesis catalysts that can be used in the present invention are, for example, those described in international patent application WO2009/020667 in the name of Elevance Renewable Science Inc., incorporated herein as reference, from page 18 paragraph [0067] to page 46 paragraph [0120].

Other patent applications that describe metathesis reactions, again in the name of the company Elevance Renewable Science Inc., are international patent application WO2010/062958, which describes a metathesis reaction followed by a hydrogenation of hydrocarbon cuts up to $C_{16}$, for obtaining jet-fuel and patent application WO2011/046872 which describes the hydrogenation of the olefinic cut coming from a metathesis reaction for obtaining biofuels such as diesel, naphtha and jet-fuel.

American patent application US20120255222, again in the name of Elevance Renewable Science Inc., claims the production of additives for improving the cold flow properties of fuels through a metathesis step. These additives can in fact be added to diesel for improving its properties.

In the present invention, the separation step (b) can be carried out by distillation.

The hydrodeoxygenation process of step (d) is preferably carried out with hydrogen in the presence of a hydrodeoxygenation catalyst; and/or the hydroisomerization process of phase (d) is carried out with hydrogen in the presence of a hydroisomerization catalyst.

The hydrodeoxygenation and hydroisomerization processes effected in the present invention and the hydrodeoxygenation and hydroisomerization catalysts used are, for example, those described in patent applications WO2008/058664, EP1728844, WO2009/039347, WO2009/039335, WO2009039333, WO2009/158268 and in American patent application US2009/0077865, wherein all these patent documents are in the name of ENI S.p.A. and UOP 11c, and are all incorporated herein as reference.

In particular, according to what is described in patent application WO2008/058664 from page 7, line 24 to page 9, line 24, all hydrogenation catalysts known in the art comprising at least one metal selected from metals of group VIII or group VIB, appropriately supported, can be used as hydrodeoxygenation catalysts. Suitable carriers are, for example, one or more metal oxides, preferably selected from: aluminia, silica, zirconia, titania, or mixtures thereof. Suitable metals are preferably Pd, Pt or Ni or Ni—Mo, Ni—W, Co—Mo or Co—W pairs.

Some hydroisomerization catalysts that can be used in the present invention are exemplified from page 13, line 19 to page 24, line 21 of WO2008058664.

The possible transesterification reaction carried out in step c) with an alcohol selected from methanol, ethanol or mixtures thereof, so as to obtain a mixture of methyl and/or ethyl esters and glycerol, is carried out according to any of the methods known in the art. In this case, the subsequent separation of the glycerol and saturated and unsaturated esters, is effected according to any of the methods known in the art, for example by means of distillation.

DETAILED DESCRIPTION OF THE FIGURES

FIG. 1

Figure 1:
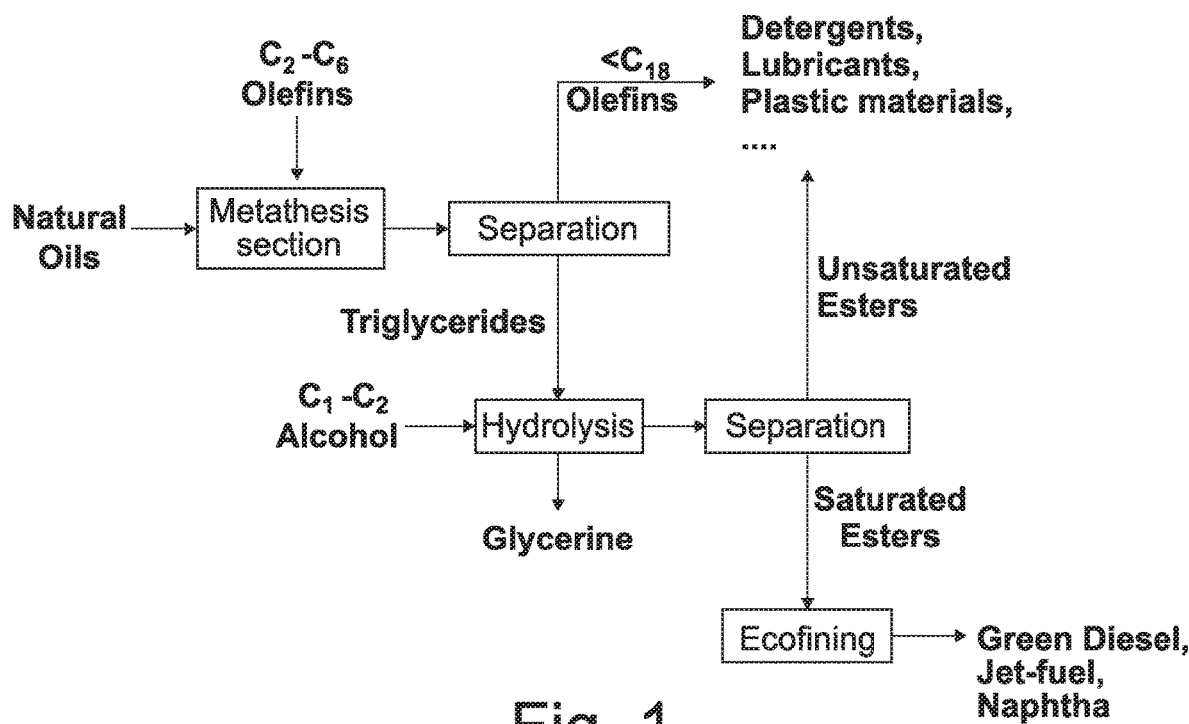
FIG. 1: the passages of the process of the invention according to a preferred embodiment, are exemplified in a block scheme (scheme 1): effecting the metathesis step, followed by separation of the olefins with less than 18 carbon atoms, hydrolysis of the fraction comprising triglycerides by the addition of $C_1$-$C_2$ alcohols, separation of the glycerine produced and unsaturated and saturated esters formed, wherein only the latter fraction is initiated to the Ecofining process for the formation of Green diesel, jet-fuel and naphtha.

As indicated in the scheme of FIG. 1, in a preferred embodiment of the process of the invention, the metathesis reaction can be effected on the mixture of triglycerides which form the starting oil with $C_2$-$C_6$, preferably $C_2$-$C_4$ olefins. The olefins having a number of carbon atoms lower than $C_{18}$ (i.e. $C_6$-$C_{18}$), formed after the metathesis reaction, which can be used as intermediates for the production of detergents, additives, lubricants and/or plastic materials or components that can be used in the field of oil explorations and productions, are easily separated by distillation from the rest of the reaction mixture which, after separation, is still composed of triglycerides of saturated fatty acids and unsaturated fatty acids which are formed as a result of the metathesis reaction. The latter are characterized in that they have an unsaturated hydrocarbon chain having a length which is less than the starting length. A transesterification reaction is then effected on these triglycerides, thus obtaining unsaturated esters of medium-chain acids (for example, $C_{10}$ if the metathesis has been effected with ethylene or ester of 9-decenoic acid, $C_{10}$-$C_{13}$ if, on the other hand, the metathesis has been effected with 1-butene, etc.) and esters of saturated fatty acids, mainly $C_{16}$ and $C_{18}$, initially present in the oil and which have remained unaltered through the metathesis reaction. Again, the difference in the boiling points allows an easy separation of the unsaturated esters from the saturated esters. The latter are sent to the hydrotreating process, or to the Ecofining process described above as a two-step process, wherein the first step consists of a hydrogenation/deoxygenation reaction (hydrodeoxygenation), whereas the second step is a hydroisomerization/cracking step.

The treatment of a composition of $C_{16}$ and $C_{18}$ methyl esters with respect to the treatment of lipids or glycerides (i.e. glycerine esters) minimizes the undesired formation of propane (mainly deriving from the direct hydrogenation of glycerine), obtaining a narrower distribution of the products with greater applicative advantages.

Figure 2:
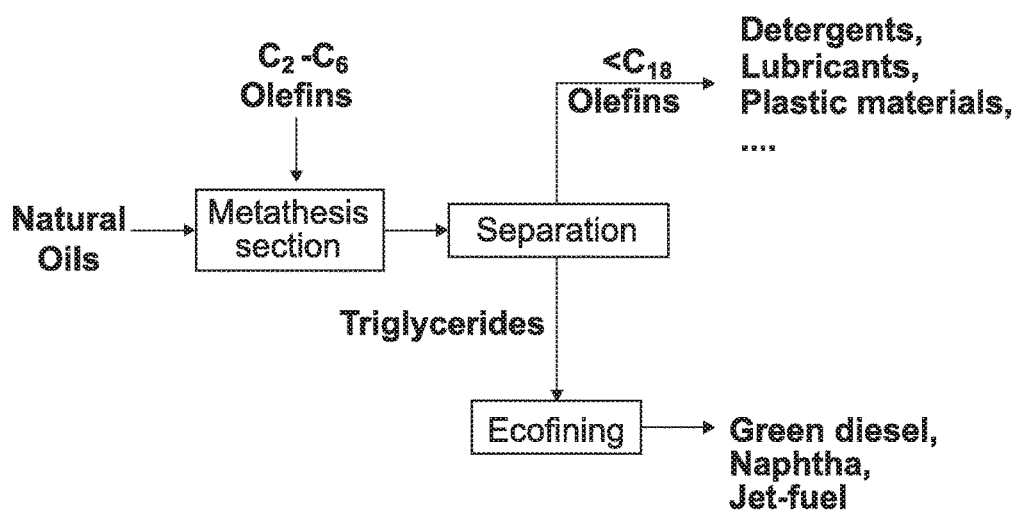
FIG. 2: the passages of the process of the invention according to another preferred embodiment, are exemplified in a block scheme (scheme 2): effecting the metathesis step, followed by separation of the olefins with less than 18 carbon atoms, Ecofining process for the formation of Green diesel, naphtha and jet-fuel.

The output of the metathesis section, in fact, becomes richer in the $C_{16}$ saturated component. The typical characteristics of the second Ecofining step (hydroisomerization, cracking), nevertheless, broadens the range of products leading to the formation of jet-fuel (prevalent), naphtha and diesel having improved engine performances.
FIG. 2

Analogously to what is described for FIG. 1, in a preferred embodiment of the process of the invention, the metathesis reaction can be carried out on the mixture of triglycerides forming the starting oil with $C_2$-$C_6$, preferably $C_2$-$C_4$ olefins. The olefins having a number of carbon atoms lower than $C_{18}$ (i.e. $C_6$-$C_{18}$), formed after the metathesis reaction, which can be used as intermediates for the renewable production of detergents, additives, lubricants and/or plastic materials or components that can be used in the field of oil explorations and productions, are easily separated by distillation from the rest of the reaction mixture which, after separation, is still composed of triglycerides of saturated fatty acids and unsaturated fatty acids which are formed as a result of the metathesis reaction. The latter are characterized in that they have an unsaturated hydrocarbon chain having a length which is less than the starting length.

This mixture can be sent directly to hydrocracking, or to the Ecofining process described above as a two-step process, wherein the first step consists of a hydrogenation/deoxygenation reaction (hydro-deoxygenation), whereas the second step is a hydroisomerization/cracking step which, due to the presence of acids having a $C_{10}$-$C_{13}$ chain, again produces not only a diesel cut but also naphtha and jet-fuel.

In view of what is described above, the process of the present invention has the following advantages:
a complete upgrading of the starting renewable biomass, with a specific production of renewable products to be used in the field of both intermediates and fine chemistry, and also in refining;
lower costs (OPEX—Operating Expenditure) in the Ecofining section, thanks to a reduction in the hydrogen consumption due to a decrease/absence of instaurations on the chain of the esters sent to said process;
improvement in the same hydrotreating section (Ecofining) as the feedstock is already pretreated and purified in the metathesis section, with a consequent reduction in investments (CAPEX—Capital Expenditure) and OPEX;
lower production of propane in the ecofining section due to the absence of glycerine derivatives in the feedstock;
maximization of the range of products to be used in the field of biofuels as they are component products useful in the field of naphtha, jet-fuel and diesel.

Some embodiment examples of the present invention are provided hereunder for illustrative but non-limiting purposes.

EXAMPLES

Example 1

According to the Scheme of FIG. 1

1 ton of palm oil, consisting of about 49% of myristic, palmitic and stearic derivatives (saturated components) and 41% of oleic acid, 10% of linoleic acid, is sent to a metathesis section with ethylene in excess at a pressure of 10 bar (stoichiometric consumption of 41 kg of ethylene). The reaction is carried out at 60° C. for about 1-1.5 hours in the presence of 100 ppm of metathesis catalyst based on ruthenium. After separation of the catalyst, the reaction mixture is distilled according to the known techniques, so as to separate about 200 kg of 1-decene and 32 kg of 1-heptene. The bottom mixture is sent to a hydrolysis section with methanol (60° C., about 2 hours of residence time, catalyst NaOMe 1% in MeOH) obtaining about 108 kg of glycerine, 330 kg of methyl ester of 9-decenoic acid, and about 470 kg of methyl esters of saturated acids $C_{16}$-$C_{18}$ (85% of $C_{16}$ ester). The 470 kg of saturated esters are separated by distillation and sent to an Ecofining section, obtaining about 375 kg of components suitable for being used in the field of biofuels of the jet-fuel type, diesel and naphtha. The components 1-decene, 1-heptene and methyl ester of 9-decenoic acid are used in the field of the production of bio-chemicals (intermediates which can be used for the production of detergents, additives, lubricants and/or plastic materials or components which can be used in the field of oil explorations and productions).

The invention claimed is:
1. A process for producing olefinic compounds and a hydrocarbon fuel or a fraction thereof, the process comprising:
   (a) subjecting to metathesis reaction a mixture of glycerides having at least one unsaturated hydrocarbon chain with at least one $C_2$-$C_6$ monoolefin in the presence of a metathesis catalyst, to obtain a mixture of glycerides having at least one unsaturated hydrocarbon chain with a carbon length less than an initial carbon length, and a mixture of $C_6$-$C_{18}$ olefins;
   (b) separating the mixture of $C_6$-$C_{18}$ olefins from the mixture of glycerides obtained by step (a);
   (c) subjecting the mixture of glycerides obtained by step (b) to a transesterification reaction with an alcohol selected from the group consisting of methanol, ethanol and mixtures thereof, to obtain a mixture of methyl esters, ethyl esters, or both, and glycerol;
   (c') separating the glycerol from the mixture of methyl esters, ethyl esters, or both; and then

(c") separating methyl esters, ethyl esters, or both, having an unsaturated hydrocarbon chain from methyl esters, ethyl esters, or both, having a saturated hydrocarbon chain in the mixture; and (d) hydrodeoxygenating a stream consisting essentially of the methyl esters, ethyl esters, or both, having a saturated hydrocarbon chain, obtained by step (c") to produce an effluent and then hydroisomerizing the effluent to obtain the hydrocarbon fuel or a fraction thereof.

2. The process of claim 1, wherein the hydrocarbon fuel is selected from the group consisting of a diesel fuel, a naphtha fuel, an aviation petrol, and mixtures thereof.

3. The process of claim 1, wherein the glycerides having at least one unsaturated hydrocarbon chain in the mixture in step (a) are glycerides of vegetable or animal origin or of microbial origin.

4. The process of claim 3, wherein the glycerides of vegetable or animal origin or of microbial origin are mono or polyunsaturated glycerides of fatty acids having at least one $C_{12}$-$C_{24}$ hydrocarbon chain.

5. The process of claim 3, wherein the glycerides are in the form of a vegetable oil, a recycled oil from a food industry, a recycled fat from a food industry, a lipid from a seaweed, an animal oil, an animal or mixtures thereof.

6. The process of claim 1, wherein the at least one $C_2$-$C_6$ monoolefin is selected from the group consisting of ethylene, propene, 1-butene, but-2-ene, 2-methyl-propene, and mixtures thereof.

7. The process of claim 1, wherein, in step (a), a molar ratio of double bonds of the mixture of glycerides having at least one unsaturated hydrocarbon chain and double bonds of the at least one $C_2$-$C_6$ monoolefin ranges from 1:0.1 to 1:20.

8. The process of claim 1, wherein step (a) occurs at a temperature from 20 to 120° C., for a period of time from 0.5 to 6 hours.

9. The process of claim 1, wherein step (a) occurs at a pressure of between 1 and 30 bars.

10. The process of claim 1, wherein the metathesis catalyst is a carbene complex of a transition metal of Group 8.

11. The process of claim 1, wherein separation in step (b) occurs by distillation.

12. The process of claim 1, wherein said hydrodeoxygenating in step (d) occurs with hydrogen in the presence of a hydrodeoxygenation catalyst.

13. The process of claim 12, wherein the hydrodeoxygenation catalyst comprises at least one metal of group VIII or of group VIB.

14. The process of claim 12, wherein the hydrodeoxygenation catalyst is supported on at least one metallic oxide.

15. The process of claim 1, wherein the said hydroisomerizing in step (d) occurs with hydrogen in the presence of a hydroisomerization catalyst.

16. The process of claim 15, wherein the hydroisomerization catalyst comprises at least one metal of group VIII and an acid-containing support.

17. The process of claim 1, wherein the glycerides are triglycerides.

18. The process of claim 1, wherein the at least one $C_2$-$C_6$ monoolefin is a $C_2$-$C_4$ monoolefin.

19. The process of claim 1, wherein the glycerides are in the form of a vegetable oil and said vegetable oil is selected from the group consisting of sunflower, rapeseed, canola, palm, soya bean, hemp, olive, linseed, mustard, peanut, castor, coconut and tall oil.

20. The process of claim 1, wherein the glycerides are in the form of a fat and said fat is selected from the group consisting of lard, lard cream, tallow, and milk fat.

21. A process for producing olefinic compounds and a hydrocarbon fuel or a fraction thereof, the process comprising:

(a) subjecting to metathesis reaction a mixture of glycerides having at least one unsaturated hydrocarbon chain with at least one $C_2$-$C_6$ monoolefin in the presence of a metathesis catalyst, to obtain a mixture of glycerides having at least one unsaturated hydrocarbon chain with a carbon length less than an initial carbon length, and a mixture of $C_6$-$C_{18}$ olefins;

(b) separating the mixture of $C_6$-$C_{18}$ olefins from the mixture of glycerides obtained by step (a);

(c) subjecting the mixture of glycerides obtained by step (b) to a transesterification reaction with an alcohol selected from the group consisting of methanol, ethanol and mixtures thereof, to obtain a mixture of methyl esters, ethyl esters, or both, and glycerol;

(c') separating the glycerol from the mixture of methyl esters, ethyl esters, or both; and then (c") separating methyl esters, ethyl esters, or both, having an unsaturated hydrocarbon chain from methyl esters, ethyl esters, or both, having a saturated hydrocarbon chain in the mixture; and (d) hydrodeoxygenating a stream consisting of the methyl esters, ethyl esters, or both, having a saturated hydrocarbon chain, obtained by step (c") to produce an effluent and then hydroisomerizing the effluent to obtain the hydrocarbon fuel or a fraction thereof.

* * * * *